United States Patent
Kim et al.

(10) Patent No.: US 11,694,360 B2
(45) Date of Patent: Jul. 4, 2023

(54) CALIBRATING 3D MOTION CAPTURE SYSTEM FOR SKELETAL ALIGNMENT USING X-RAY DATA

(71) Applicant: Ssam Sports, Inc., Saddle River, NJ (US)

(72) Inventors: Sang J. Kim, Saddle River, NJ (US); Laszlo Kustra, Budapest (HU)

(73) Assignee: SSAM SPORTS, INC., Saddle River, NJ (US)

( * ) Notice: Subject to any disclaimer, the term of this patent is extended or adjusted under 35 U.S.C. 154(b) by 293 days.

(21) Appl. No.: 17/089,040

(22) Filed: Nov. 4, 2020

(65) Prior Publication Data
US 2021/0134011 A1    May 6, 2021

Related U.S. Application Data

(60) Provisional application No. 62/931,602, filed on Nov. 6, 2019.

(51) Int. Cl.
| | |
|---|---|
| G06K 9/00 | (2022.01) |
| A61B 8/13 | (2006.01) |
| G06T 7/80 | (2017.01) |
| G06T 7/00 | (2017.01) |
| G06T 7/70 | (2017.01) |
| A61B 5/00 | (2006.01) |

(Continued)

(52) U.S. Cl.
CPC ............ *G06T 7/80* (2017.01); *A61B 5/0077* (2013.01); *A61B 5/1121* (2013.01); *A61B 5/1128* (2013.01); *A61B 6/461* (2013.01); *A61B 6/469* (2013.01); *G06T 7/0012* (2013.01); *G06T 7/70* (2017.01); *G06T 2200/24* (2013.01); *G06T 2207/10116* (2013.01); *G06T 2207/30008* (2013.01)

(58) Field of Classification Search
CPC .............. G06K 9/00; A61B 6/563; A61B 8/13
USPC ........ 382/100, 103, 106–107, 128–132, 168, 382/173, 181, 189, 219, 254, 276, 286, 382/291, 305, 312, 154; 600/407, 443
See application file for complete search history.

(56) References Cited

U.S. PATENT DOCUMENTS

| | | | |
|---|---|---|---|
| 10,685,394 B2 * | 6/2020 | Suzuki | G06Q 30/0643 |
| 2015/0094564 A1 * | 4/2015 | Tashman | A61B 6/563 600/407 |

(Continued)

OTHER PUBLICATIONS

International Preliminary Report on Patentabiltiy for International Application No. PCT/US2020/058979, dated May 19, 2022, 7 pages.

(Continued)

*Primary Examiner* — Seyed H Azarian
(74) *Attorney, Agent, or Firm* — Lowenstein Sandler LLP

(57) ABSTRACT

A processing device receives, from a three-dimensional (3D) motion capture system, initial data representing an initial orientation of a subject user's body in an initial position. The processing device further receives x-ray data representing at least the portion of the subject user's body in the initial position. The processing device determines an actual orientation of at least one bone or joint from the portion of the subject user's body in the initial position as represented in the x-ray data and calibrates the initial orientation of the 3D motion capture system to reflect the actual orientation of the at least one bone or joint in the initial position.

17 Claims, 6 Drawing Sheets

(51) Int. Cl.
    *A61B 5/11*          (2006.01)
    *A61B 6/00*          (2006.01)

(56) References Cited

U.S. PATENT DOCUMENTS

| | | | |
|---|---|---|---|
| 2015/0094584 A1* | 4/2015 | Abe | A61B 8/483 |
| | | | 600/443 |
| 2016/0258779 A1* | 9/2016 | Hol | G01P 21/00 |
| 2016/0278868 A1* | 9/2016 | Berend | A61B 5/1127 |

OTHER PUBLICATIONS

International Search Report and Written Opinion for International Application No. PCT/US2020/058979, dated Feb. 4, 2021, 12 pages.

* cited by examiner

CALIBRATING 3D MOTION CAPTURE SYSTEM FOR SKELETAL ALIGNMENT USING X-RAY DATA

RELATED APPLICATIONS

This application claims the benefit of U.S. Provisional Patent Application No. 62/931,602, filed Nov. 6, 2019, the entire contents of which are hereby incorporated by reference herein.

TECHNICAL FIELD

The present disclosure is generally related to computer systems, and is more specifically related to calibrating a 3D motion capture system for skeletal alignment using x-ray data.

BACKGROUND

Two dimensional (2D) imaging is widely used by doctors and other health professionals to analyze human motion in sports and health applications because 2D imaging is relatively simple, inexpensive and widely available. Three dimensional (3D) motion visualization is much more advanced and provides data, multiple viewing angles, and digital data analysis that 2D imaging cannot provide. 3D systems can provide useful information of angles, speed, orientation, etc. which can be used to identify poor movement for performance or health. 3D motion visualization, however, requires sensors or markers and technology that may take longer to set up and is more expensive.

BRIEF DESCRIPTION OF THE DRAWINGS

The present disclosure is illustrated by way of example, and not by way of limitation, and can be more fully understood with reference to the following detailed description when considered in connection with the figures in which.

DETAILED DESCRIPTION

Figure 1:
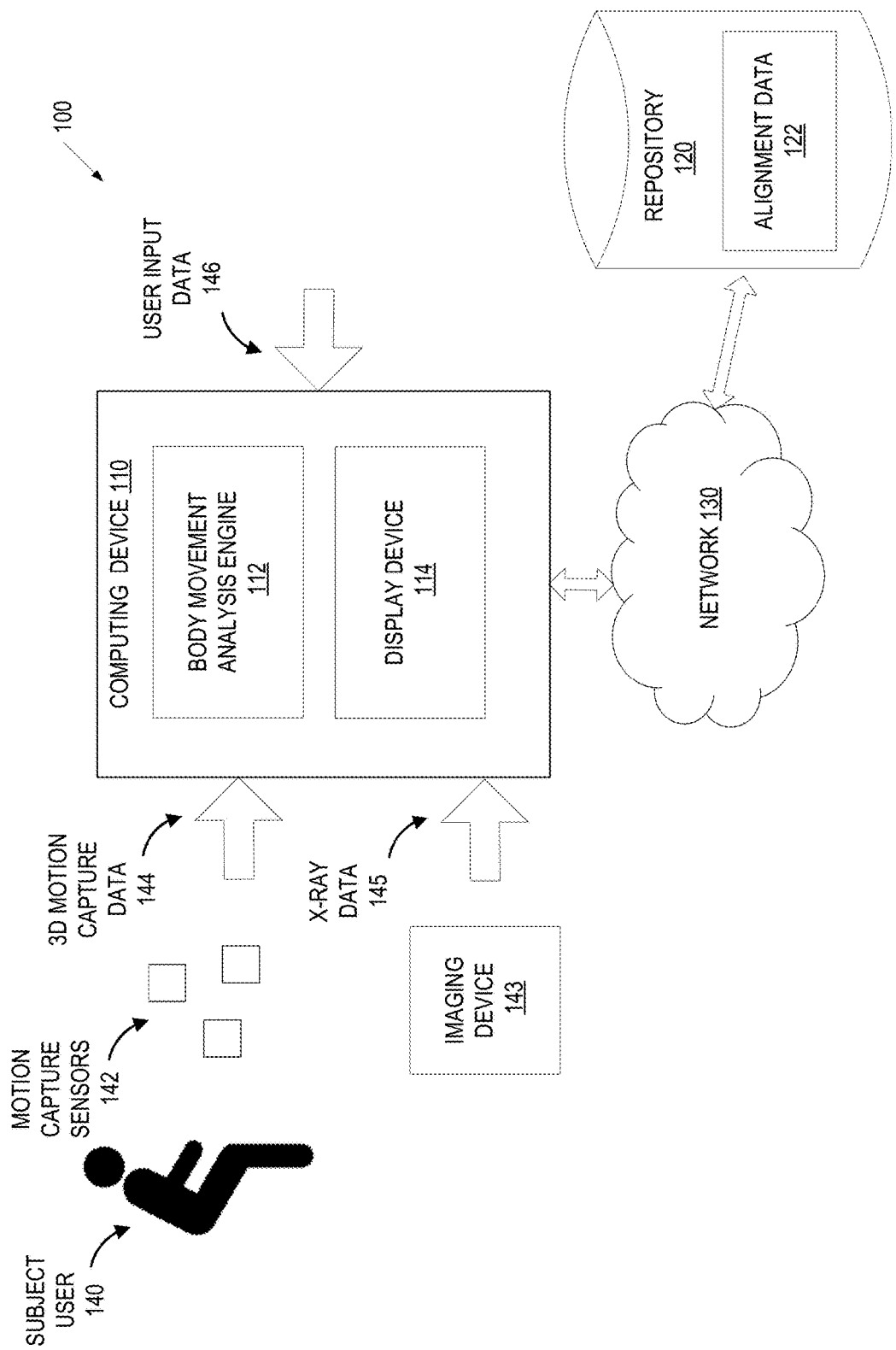
FIG. 1 depicts a high-level component diagram of an illustrative system architecture, in accordance with one or more aspects of the present disclosure.

Embodiments for calibrating a 3D motion capture system for skeletal alignment using x-ray data are described. The technology described herein can be used to derive precise skeletal alignment and movement data using a combination of x-ray data and a 3D motion capture system. Three-dimensional (3D) motion capture systems derive their information from markers, cameras, or sensors placed on the outside of the subject user's body. A calibration method is used to create a reference frame for the movement of the body, so that the relative movement of the sensors and body can be tracked and analyzed. Certain implementations attempt to align the sensors relative to specific portions of the subject user's body (e.g., the bones of the user's skeleton). Since people have flesh, muscles, etc. in between the skeleton and the sensors affixed to the skin, it can be difficult to know the exact alignment of the sensors relative to the skeleton itself and, therefore, difficult to measure the precise angles of movement of the skeleton using the sensors. Often times an assumption is made about that orientation of the skeleton inside the body in order to generate the reference frame. While this is adequate for certain implementations, other implementations require a more precise alignment of the motion capture sensors and the skeleton. Without this precise alignment, the reference frame can be miscalculated the 3D motion capture analysis can be inaccurate and/or misleading.

Of course the technology does exist to see inside the subject user's body. Two-dimensional (2D) radiographs (i.e., x-ray images) or a computerized tomography scan can capture a user's bones or joints in certain static positions (e.g., supine, standing, and/or sitting). These static images are less than ideal for motion capture analysis due to their imprecise nature, their ability to capture only a brief moment in time which can be quite variable, and their limited reproducibility and consistency possibly leading to measurement error. The x-ray images generally only capture a single plane (e.g., the sagittal plane, the coronal plane) and do not offer a 3D perspective. In addition, the static images cannot be used to detect rotational (e.g., axial or transverse plane) or coupled orientation changes.

The implementations described herein address the above and other considerations by calibrating a 3D motion capture system for skeletal alignment using x-ray data. By capturing x-ray data to get precise skeletal alignment and then combining this x-ray data with 3D motion capture data to track movement of the subject user's body, the system described herein can obtain precise skeletal angles and positions during the movement. In one embodiment, the subject user stands in a known pose (i.e., a calibration pose) and one or more x-ray images are taken from one or more angles. For example, an x-ray can be taken from the front of the subject user and then from one or more of the other sides. This x-ray image(s) can then be used to determine the position (i.e., angles) of certain body parts (e.g., portions of the user's skeleton) in that known pose. For example, if an x-ray is taken from the front and the side, the resulting image will illustrate the tilt, obliquity, and rotation of the pelvis or other bone or body part in that known pose. In one embodiment, the system can receive user input (e.g., from a technician, doctor, or other user) identifying the portions of the subject user's skeleton that are of interest and can determine one or more corresponding measurements (e.g., the angles of orientation of the skeleton relative to some global reference frame, or relative to some other element, such as a 3D motion capture sensor).

As described above, conventional motion capture systems either assume the angles of the skeleton are zero (or some other default value) in the calibration pose or use the measurements from placed on the outside of the body which assume the skeleton is similarly aligned. In embodiments of the present disclosure, however, x-ray data showing the true orientation of the skeleton is received as an input to the 3D motion capture system, and can be used to offset the position of the skeleton. For example, at least one calibration pose is an attention pose where each bone is considered to be in a neutral position (i.e., zero degrees of rotation on all three axes). In this pose, the joints are also considered neutral (i.e., zero degrees of bending). By using the actual skeletal alignment data obtained from the x-ray images and offsetting the skeletal data in the same reference pose captured by the 3D motion capture system, the 3D motion capture system now has a much more accurate skeletal reference frame to capture precise skeletal angles throughout movement of the subject user's body. The input data from the x-ray images is incorporated into the 3D motion capture system to define the starting skeletal alignment before any calculations are made. The data from the x-ray images of the subject user in the reference pose can be saved into the 3D motion capture system and all motion capture data and results can be calculated based on movement relative to the reference pose.

This adjustment can be very important for certain applications. For example, if the subject user were to perform a simple motion, such as a deep squat (i.e., starting in a standing position and bending the knees and waist in a deep squat), most sensor based systems must assume the pelvis initially had zero degrees of rotation, tilt, and obliquity at the starting position. During movement and at the bottom of the deep squat, the system can produce relative angles of the pelvis, but only in relation to the assumed starting angles of the pelvis. The x-ray data input to the system however, might show that the subject user actually has 10 degrees of anterior tilt and 3 degrees of left side obliquity, for example, in the starting position. If this case, the positional data of the pelvis could be quite misleading at the bottom of the deep squat because the initial reference orientation was not correct.

In one embodiment, one feature of the system is to analyze the subject user's movement based on the position of the pelvis at the bottom of the deep squat. With an incorrect reference orientation, the 3D motion capture system would be providing inaccurate results. Since the positions and movement of the pelvis, femur, and hips, for example, move on all three planes simultaneously, the system cannot simply offset the result data by the initial differences of position provided by the x-ray data and the assumptions made. However, by combining the actual known positions of the skeleton provided by the x-ray data, inputting those positions into the 3D motion capture system before any movement is made, and then performing 3D calculations of the motion data with the actual positions of the skeleton, the system can more accurately determine the angles and positions of the skeleton during all parts of the movement, leading to much more precise and useful analysis.

FIG. 1 depicts a high-level component diagram of an illustrative system architecture 100, in accordance with one or more aspects of the present disclosure. System architecture 100 includes a computing device 110 and a repository 120 connected to a network 130. Network 130 may be a public network (e.g., the Internet), a private network (e.g., a local area network (LAN) or wide area network (WAN)), or a combination thereof.

The computing device 110 may be configured to perform dynamic 3D motion capture for body motion analysis, skeletal alignment, and/or other analyses. In one embodiment, computing device 110 may be a desktop computer, a laptop computer, a smartphone, a tablet computer, a server, or any suitable computing device capable of performing the techniques described herein. In one embodiment, computing device 110 receives 3D motion capture data 133 from a 3D motion capture system, which can be implemented in a variety of ways. In one embodiment, a plurality of motion capture sensors 142, which may be affixed to one or more body parts of a subject user 140 while they are performing a physical movement, capture 3D motion capture data 144 corresponding to the subject user 140. Depending on the implementation, the motion capture sensors 142 can be attached externally to the skin of the subject user 140 or internally to the bones of the subject user 140. In other embodiments, the motion capture sensors 142 may be affixed to any relevant object being manipulated by the subject user 140 while performing the physical movement, such as to a golf club, baseball bat, tennis racquet, crutches, prosthetics, etc. The 3D motion capture data 144 may be received by the computing device 110. In one embodiment, the 3D motion capture system is integrated within computing device 110, and so the 3D motion capture data 144 is received internally.

When the 3D motion capture system is external to computing device 110, the 3D motion capture data 144 may be received in any suitable manner. For example, the motion capture sensors 142 may be wireless inertial sensors, each including for example, a gyroscope, magnetometer, accelerometer, and/or other components to measure sensor data including relative positional data, rotational data, and acceleration data. The 3D motion capture data 144 may include this sensor data and/or other data derived or calculated from the sensor data. The motion capture sensors 142 may transmit the 3D motion capture data 144 including, raw sensor data, filtered sensor data, or calculated sensor data, wirelessly to computing device 110 using internal radios or other communication mechanisms. In other embodiments, the 3D motion capture system may not utilize motion capture sensors 142 and other systems may be used to capture 3D motion capture data 144, such as an optical system, using one or more cameras including a marker-based camera system or a marker-less camera system, a mechanical motion system, an electro-magnetic system, an infra-red system, etc. In addition, in other embodiments, the 3D motion capture data 144 may have been previously captured and stored in a database or other data store. In this embodiment, computing device 110 may receive the 3D motion capture data 144 from another computing device or storage device where the 3D motion capture data 144 is maintained. In still other embodiments, the 3D motion capture data 144 may be associated with other users besides or in addition to subject user 140 performing a physical activity.

Figure 2:
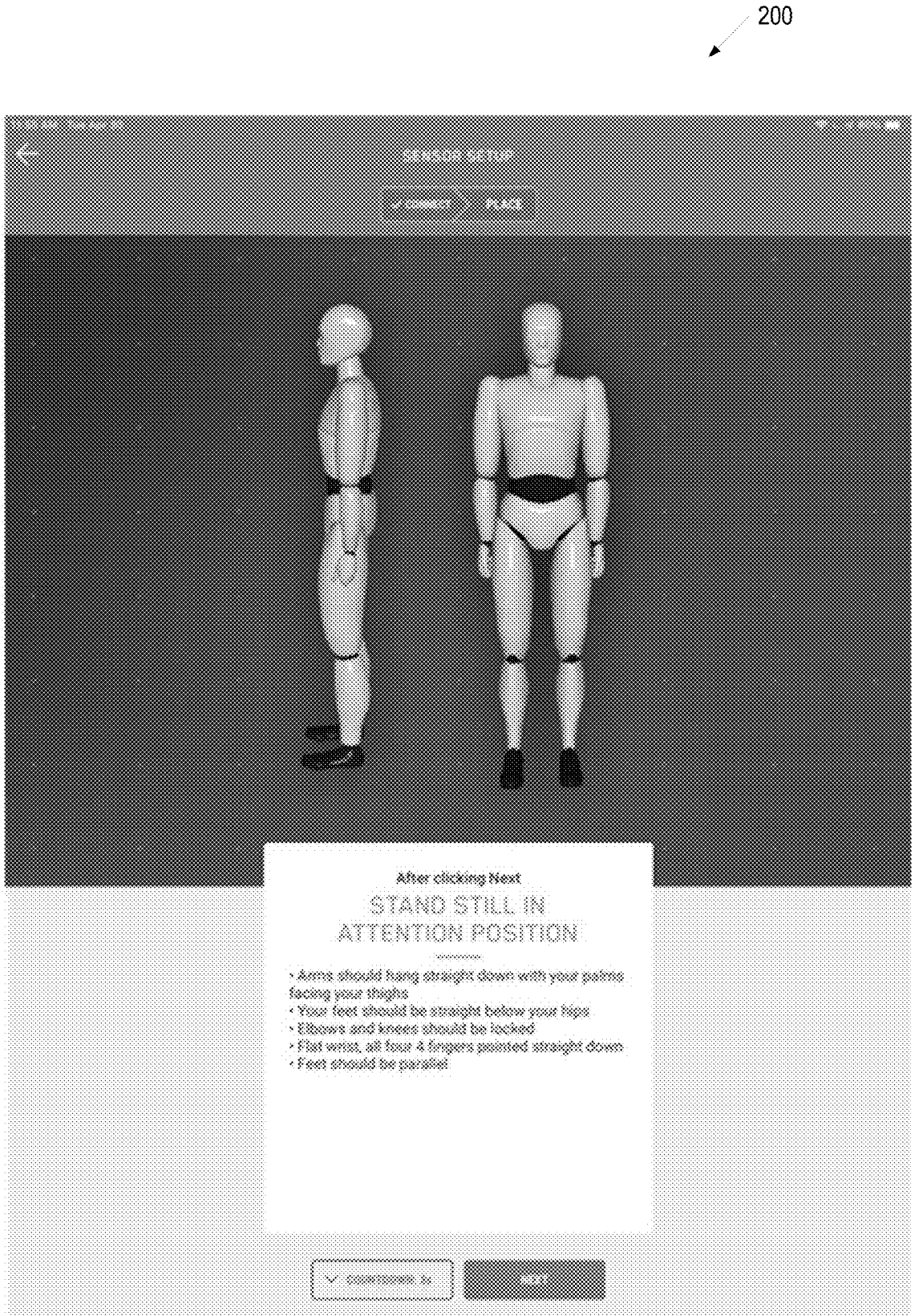
FIG. 2 depicts a visualization of the subject user in one possible initial position, in accordance with one or more aspects of the present disclosure.

In one embodiment, motion capture sensors 142 capture the 3D motion capture data 144 while the subject user 140 is in an initial position (i.e., a calibration position or pose). While in the initial position, the subject user's body, or at least a portion of the body, can remain still or nearly still, so that the 3D motion capture data 144 can include initial data representing an initial orientation of the motion capture sensors 142. FIG. 2 depicts a visualization 200 of subject user 140 in one possible initial position, in accordance with one or more aspects of the present disclosure. The visualization 200 illustrates the "attention" position, which can be used to calibrate the motion capture sensors 142 affixed to the body of subject user 140. In the attention position, subject user 140 can be standing with arms hanging straight down with palms facing the thighs. The feet can be flat on the ground, parallel, and straight below the hips. Elbows and knees can be locked, with wrists flat, and all fingers pointing straight down. In other embodiments, other initial positions can be used.

In one embodiment, the motion capture sensors 142 are placed on the subject user's body, in an attempt to align with at least one bone or joint while subject user 140 is in the initial position. For example, one or more motion capture sensors 142 can be placed on the hips and/or back of subject user 140 in approximate alignment with the pelvis. Due to the intervening layers of skin, muscle, or other body tissue, there may be a difference between the alignment of the motion capture sensors 142 and the alignment of the pelvis of subject user 140. Thus, the initial data representing the initial orientation of the motion capture sensors 142 may not accurately represent the orientation of the pelvis when the subject user is in the initial position. For example, the initial data includes first values of tilt and rotation measured by the motion capture sensors 142. In one embodiment, in the absence of any external reference frame, these first values representing the initial orientation of motion capture sensors 142 include zero degrees of tilt and rotation on all three axes (e.g., 0 degrees forward tilt, 0 degrees side tilt, 0 degrees rotation). As noted, these first values may not accurately represent the actual orientation of the pelvis, or other bone or joint, of subject user 140.

In one embodiment, motion capture sensors 142 further capture the 3D motion capture data 144 while the subject user 140 is performing a physical activity or a physical movement. The physical activity can be for example, swinging a golf club, throwing a ball, running, walking, jumping, sitting, standing, or any other physical activity. When performing the physical activity, the subject user 140 may make one or more physical body movements that together enable performance of the physical activity. For example, when performing a physical activity, such as standing form a sitting position, walking, or other activity, the user may rotate their hips and shoulders, swing their arms, hinge their wrists, turn their pelvis, etc., each of which can be considered a separate body movement associated with performing the physical activity. Each physical activity may have its own unique set of associated body movements. Each physical movement can involve motion of a bone or joint of the subject user 140. Thus, the 3D motion capture data 144 can include continuous motion capture data representing dynamic motion of at least one of a bone or joint of the subject user 140 while they are performing the physical movement. The continuous nature can differentiate the 3D motion capture data 144 from a mere static image captured at a single point in time.

In one embodiment, computing device 110 further receives x-ray data 145, such as from an imaging device 130. Imaging device 130 can include for example, radiography equipment, such as an x-ray generator and detector, computerized tomography equipment, or other imaging equipment. The x-ray data 145 can include a digital data stream representing the x-ray image of at least a portion of the body of subject user 140, captured by imaging device 143. For example, while subject user 140 is in the initial position, such as the attention pose described above, imaging device 130 can capture the x-ray image, and corresponding x-ray data 145 can be sent to computing device 110.

In one embodiment, computing device 110 may include body movement analysis engine 112. The body movement analysis engine 112 may include instructions stored on one or more tangible, machine-readable storage media of the computing device 110 and executable by one or more processing devices of the computing device 110. In one embodiment, body movement analysis engine 112 receives the 3D motion capture data 144 of the subject user 140 performing the physical activity or physical movement and receives the x-ray data 145 of subject user 140 representing at least a portion of subject user's body while in the initial position. Body movement analysis engine 112 can use x-ray data 145 to refine the motion capture data 344 and improve the readings of motion capture sensors 142.

Figure 3:
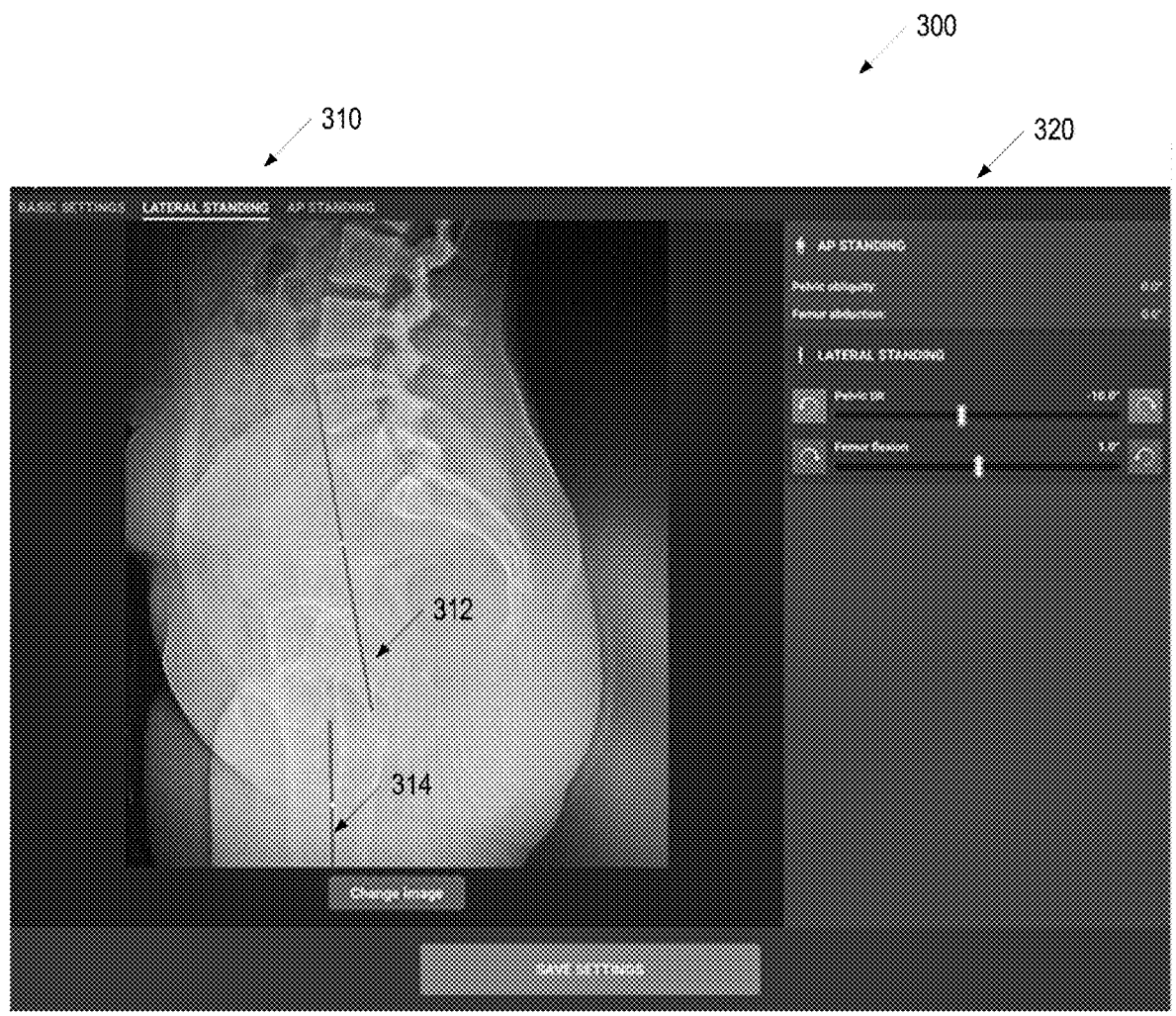
FIG. 3 depicts one example of an interface for calibrating a 3D motion capture system for skeletal alignment using x-ray data in accordance with one or more aspects of the present disclosure.

In one embodiment, body movement analysis engine 112 determines an actual orientation of at least one bone or joint from the portion of the subject user's body in the initial position, as represented in x-ray data 145. In one embodiment, body movement analysis engine 112 generates an image (i.e., an x-ray image) from the received x-ray data 145, where the image is of a portion of the body (e.g., the pelvis) of subject user 140. Body movement analysis engine 112 can cause display of the image in an interface on a display device, such as display device 114. Depending on the embodiment, the display device can be integrated within computing device 110, or can be a display device of some other device connected to network 130, or wirelessly connected directly to computing device 110 or any other computing device. FIG. 3 depicts one example of an interface 300 for calibrating a 3D motion capture system for skeletal alignment using x-ray data in accordance with one or more aspects of the present disclosure. In one embodiment, interface 300 is a graphical user interface including an image display area 310 and a user input area 320. In one embodiment, upon presenting the x-ray image in display area 310 of interface 300, body movement analysis engine 112 further receives input, such as user input data 146 via input area 320 of interface 300. A surgeon, doctor, technician, health professional, or other user, can provide user input data 146 including an indication of at least one bone or joint depicted in the x-ray image. As illustrated in FIG. 3, the user input can include an alignment indicator indicating the at least one bone or joint. In this case, alignment indicator 312 indicates the alignment of the pelvis shown in the x-ray image, and alignment indicator 314 indicates the alignment of the femur shown in the x-ray image.

Based on the alignment indicator(s), body movement analysis engine 112 can calculate an offset or offsets of the at least one bone or joint relative to a reference frame. For example, body movement analysis engine 112 can determine that alignment indicator 312 indicates a certain degree of pelvic tilt (e.g., −10 degrees) on a given axis, and that alignment indicator 314 indicates a certain degree of femur flexion (e.g., 1 degree). In one embodiment, body movement analysis engine 112 calculates these offsets in relation to a reference frame, such as an Earth-bound reference frame (i.e., 3-axis coordinate system). In other embodiments, the offsets can be defined using some other reference frame, such as a functional pelvic plane, or an anterior pelvic plane (APP) reference frame. For example, the offsets can include second values of tilt and rotation relative to the defined axes (i.e., zero degrees) of the reference frame. In one embodiment, these offsets represent the actual orientation of the at least one bone or joint in the initial position.

Referring again to FIG. 1, in one embodiment, having determined the actual orientation of the at least one bone or joint in the initial position, body movement analysis engine 112 can calibrate the initial orientation of the motion capture sensors 142, as indicated in 3D motion capture data 144, to reflect the actual orientation. In one embodiment, body movement analysis engine 112 can replace the first values of tilt and rotation measured by the motion capture sensors 142 with the second values of tilt and rotation determined from the x-ray data 145. For example, as described above, if the first values representing the initial orientation of motion capture sensors 142 include zero degrees of tilt and rotation on all three axes, body movement analysis engine can replace those first values with the second values representing the actual orientation of the at least one bone or joint (e.g., −10 degrees of forward pelvic tilt). As such, body movement analysis engine 112 can interpret movement of the body of subject user 140, as reflected in subsequently received 3D motion capture data 144, relative to the actual orientation in the initial position. Such as if body movement analysis engine 112 were attempting to analyze the amount of pelvic tilt subject user 140 achieved during the performance of a body movement (e.g., a deep squat), the amount of pelvic tilt at the bottom of the deep squat could be compared to the amount of pelvic tilt in the initial position (i.e., at the start of the deep squat). Since the initial orientation has been calibrated to reflect the actual orientation of the pelvis in the initial position, the difference between the measurements will be a more accurate representation of the actual amount of pelvic tilt achieved. In one embodiment, 3D motion capture data 144, x-ray data 145, user input data 146, and data representing the actual orientation of the at least one bone or joint as determined by body movement analysis engine can be stored as part of alignment data 122 in repository 120.

The repository 120 is a persistent storage device that is capable of storing alignment data 122 and/or other data, as well as data structures to tag, organize, and index this data. Repository 120 may be hosted by one or more storage devices, such as main memory, magnetic or optical storage based disks, tapes or hard drives, NAS, SAN, and so forth. Although depicted as separate from the computing device 110, in an implementation, the repository 120 may be part of the computing device 110 or may be directly attached to computing device 110. In some implementations, repository 120 may be a network-attached file server, while in other embodiments, repository 120 may be some other type of persistent storage such as an object-oriented database, a relational database, and so forth, that may be hosted by a server machine or one or more different machines coupled to the via the network 130.

Figure 4:
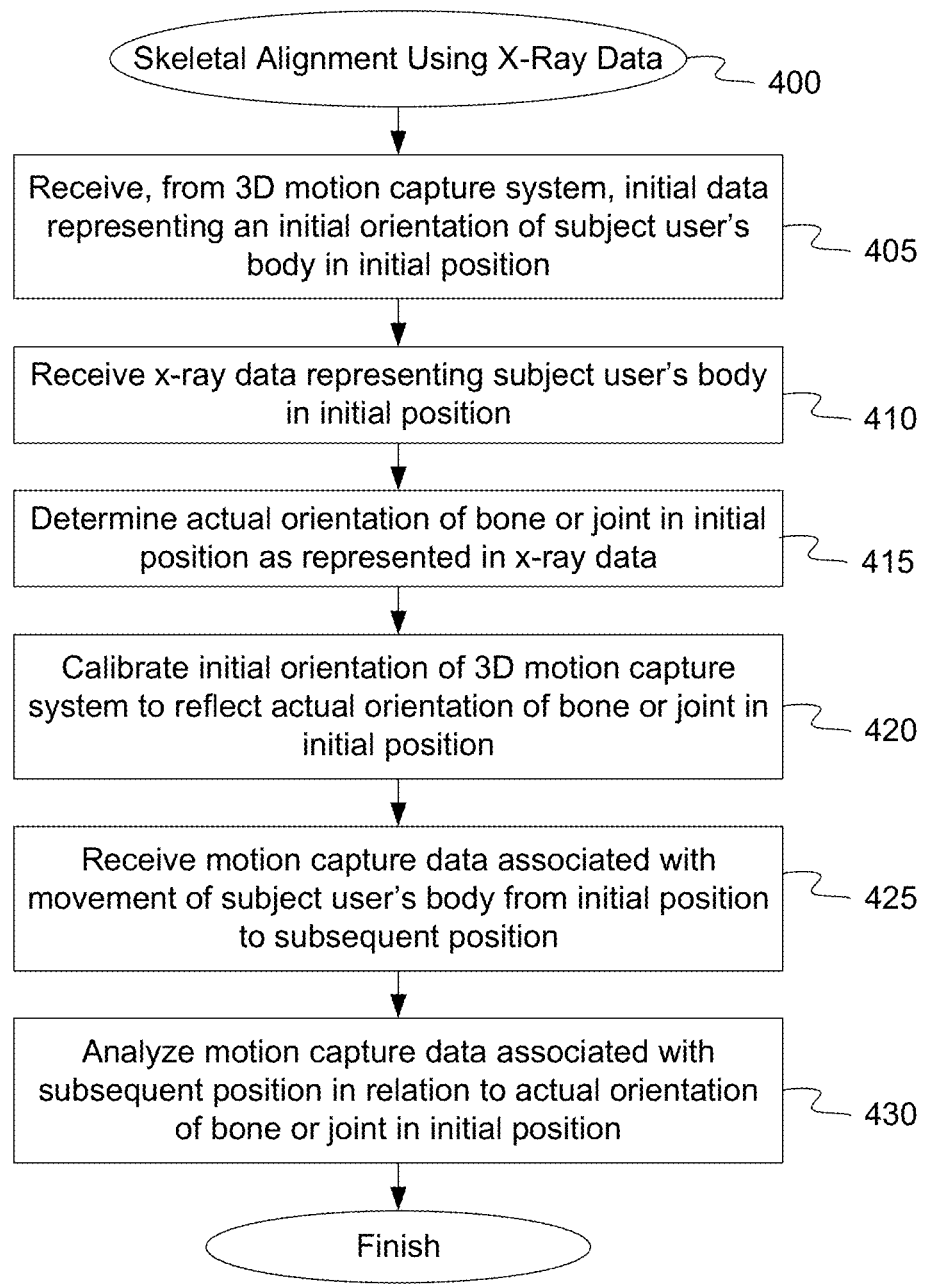
FIG. 4 is a flow diagram illustrating a method of calibrating a 3D motion capture system for skeletal alignment using x-ray data in accordance with one or more aspects of the present disclosure.

FIG. 4 is a flow diagram illustrating a method of calibrating a 3D motion capture system for skeletal alignment using x-ray data in accordance with one or more aspects of the present disclosure. The method 400 may be performed by processing logic that comprises hardware (e.g., circuitry, dedicated logic, programmable logic, microcode, etc.), software (e.g., instructions run on a processor to perform hardware simulation), firmware, or a combination thereof. In one embodiment, method 400 may be performed by computing device 110 including body movement analysis engine 112, as shown in FIG. 1.

Referring to FIG. 4, at block 405, method 400 receives, from a three-dimensional (3D) motion capture system, such as motion capture sensors 142 affixed to at least a portion of a subject user's body, initial data representing an initial orientation of the plurality of 3D motion capture sensors 142 when the subject user's body is in an initial position (e.g., the calibration position illustrated in FIG. 2). In one embodiment, the motion capture sensors are 142 calibrated to the body of the subject user 140 while the subject user 140 establishes a pose, providing a baseline orientation of the sensors on the respective body parts in a known orientation across the three axes. Computing device 110 sends a signal to the sensors to begin the recording. The subject user 140 assumes the calibration pose so that the sensors can determine the initial orientation. The sensors then send the data back the computing device 110.

At block 410, method 400 receives x-ray data 145 representing at least the portion of the subject user's body in the initial position.

At block 415, method 400 determines an actual orientation of at least one bone or joint from the portion of the subject user's body in the initial position as represented in the x-ray data 145. Additional details with respect to how the actual orientation is determined are provided below with respect to FIG. 5.

At block 420, method 400 calibrates the initial orientation of the plurality of 3D motion capture system to reflect the actual orientation of the at least one bone or joint in the initial position. Additional details with respect to how the initial orientation is calibrated are provided below with respect to FIG. 5.

At block 425, method 400 receives, from the 3D motion capture system, motion capture data 144 associated with a movement of the subject user's body from the initial position to a subsequent position (e.g., a deep squat). In one embodiment, the motion capture sensors 142 are wireless inertial sensors, each including a gyroscope, magnetometer, accelerometer, and/or other components to measure relative positional data, rotational data, acceleration data, and/or other data. The 3D motion capture data 144 includes data representing dynamic motion of at least one of a bone or a joint of the subject user 140 associated with performing the physical movement. In one embodiment, computing device 110 receives the 3D motion capture data 144 from the motion capture sensors 142 over a wireless communication link (e.g., Bluetooth). In other embodiments, the 3D motion capture data 144 may have been previously captured and stored in a database or other data store, such as repository 120. In one embodiment, the 3D motion capture data 144 is accompanied by a request or instruction to perform a movement analysis for the subject user 140. The request may be received from a user of computing device 110, from a user of a client device coupled to computing device 110 via network 130, or from some other requestor. In one embodiment, body movement analysis engine 112 receives the 3D motion capture data 144 and stores the 3D motion capture data 144 in repository 120.

At block 430, method 400 analyzes the motion capture data 144 associated with the subsequent position in relation to the actual orientation of the at least one bone or joint in the initial position.

Figure 5:
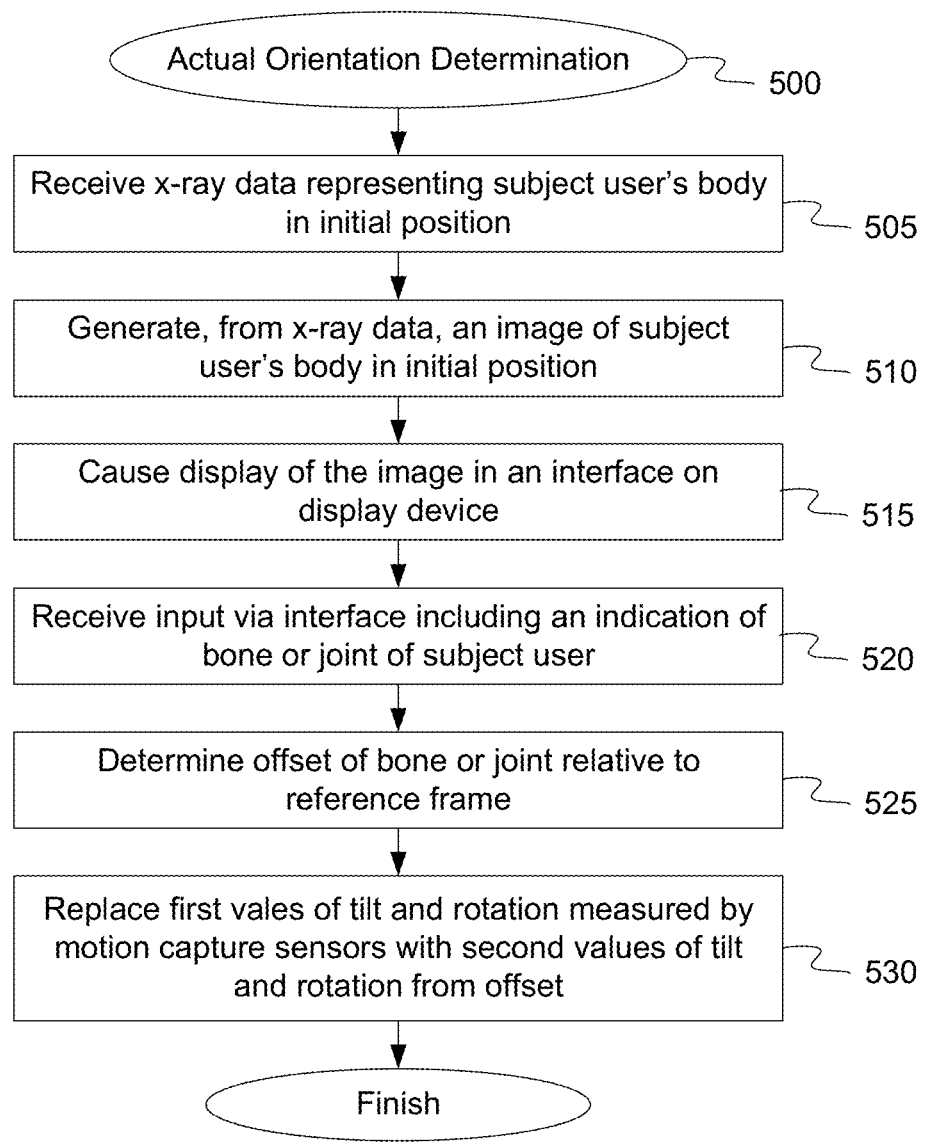
FIG. 5 is a flow diagram illustrating method of determining the actual orientation of at least one bone or joint in an initial position using x-ray data in accordance with one or more aspects of the present disclosure.

FIG. 5 is a flow diagram illustrating method of determining the actual orientation of at least one bone or joint in an initial position using x-ray data in accordance with one or more aspects of the present disclosure. The method 500 may be performed by processing logic that comprises hardware (e.g., circuitry, dedicated logic, programmable logic, microcode, etc.), software (e.g., instructions run on a processor to perform hardware simulation), firmware, or a combination thereof. In one embodiment, method 500 may be performed by computing device 110 including body movement analysis engine 112, as shown in FIG. 1.

Referring to FIG. 5, at block 505, method 500 receives x-ray data 145 representing at least the portion of the subject user's body in the initial position, as described above.

At block 510, method 500 generates, from the x-ray data 145, an image of the portion of the subject user's body in the initial position.

At block 515, method 500 causes display of the image in an interface (e.g., interface 300 of FIG. 3) on a display device 114.

At block 520, method 500 receives input via the interface 300, the input comprising an indication of the at least one bone or joint. Body movement analysis engine 112 can receive input, such as user input data 146, from a surgeon, or other health professional, including an indication of the bone or joint in the x-ray image. In one embodiment, the interface 300 includes a number of controls through which the user can provide input data 146 to indicate the bone or joint. For example, the controls can provide the ability to draw a line, such as 312 or 314 indicating the alignment of a certain bone in the x-ray image. A surgeon, radiologist, or other user can use known landmarks visible in the x-ray to position the lines. For example on the pelvis, a trained professional will know to position one end of the line on a specific part of the bone and the other on another specific part of the bone.

At block 525, method 500 determines an offset of the at least one bone or joint relative to a reference frame, wherein the offset represents the actual orientation of the at least one bone or joint in the initial position. In one embodiment, body movement analysis engine 112 can run algorithms that take the raw sensor data and compute human readable motion analysis, for example, taking quaternion sensor data and computing Euler angles relative to the three axis of rotation of bone segments. This can then be converted into joint movement data such as internal/external rotation, abduction/adduction and flexion/extension of a joint (e.g., hip, knee, shoulder, etc.), or bony segment (e.g., femur, tibia/fibula, humerus, radius ulna, vertebra, etc.), as well as joint and skeletal contact stresses and joint reaction forces. Furthermore, the bone and joint movement data can take the x-ray data 145 to make an off-set adjustment of the initial orientation. For example, the initial orientation may assume that a certain bone or other body part has zero forward or backward bend. The x-ray data 145 may provide initial forward and backward angle bends for the body parts, which can be an input parameter to provide the actual orientation of the body part from which the relative movement data of the sensors can be offset. In one embodiment, body movement analysis engine 112 can compute the angle of the lines drawn on the x-ray image to determine the initial offset. The algorithm will compute the segment and joint movements frame by frame captured by the sensors and map out the data in graph form. This information is readily accessible on the computing device right after the capture without human intervention or adjustment. The 3D motion capture sensors 142 can capture continuous movement data across multiple planes, which offers a substantial improvement over static 2D images. Conventional systems capture the body part in two positions (e.g., standing and sitting), and uses statistical models to try to extrapolate the movement, range of motion, and possible impingement. Using the techniques described herein, body movement analysis engine 112 can get actual movement, range of motion, and impingement angles from actual data without having to rely on statistical projections.

At block 530, to calibrate the initial orientation of the plurality of 3D motion capture sensors 142 to reflect the actual orientation of the at least one bone or joint in the initial position, method 500 replaces first values of tilt and rotation measured by the plurality of 3D motion capture sensors 142 with second values of tilt and rotation determined from the x-ray data 145.

Figure 6:
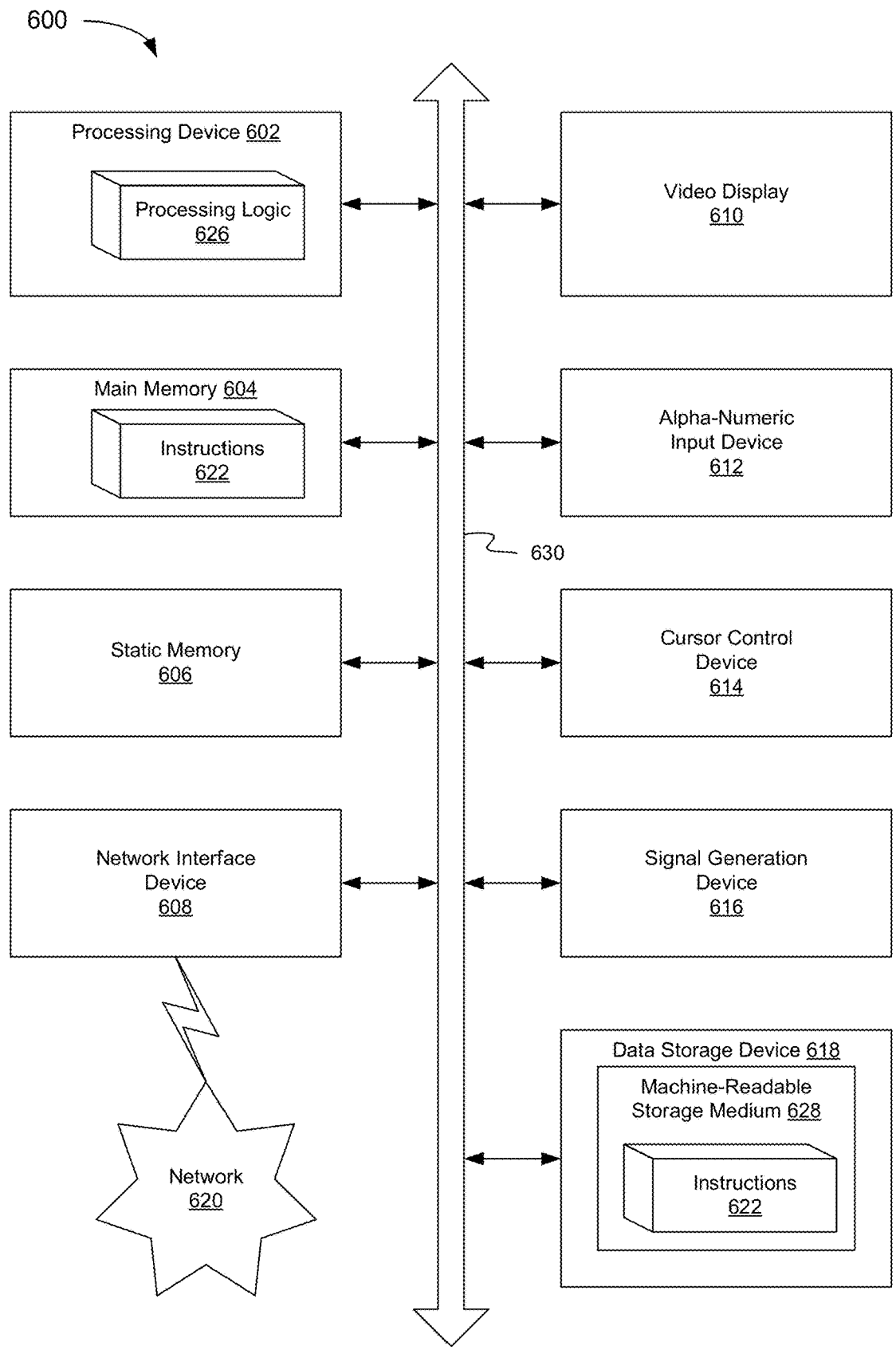
FIG. 6 depicts an example computer system which can perform any one or more of the methods described herein, in accordance with one or more aspects of the present disclosure.

FIG. 6 depicts an example computer system 600 which can perform any one or more of the methods described herein, in accordance with one or more aspects of the present disclosure. In one example, computer system 600 may correspond to a computing device, such as computing device 110, capable of executing body movement analysis engine 112 of FIG. 1. The computer system 600 may be connected (e.g., networked) to other computer systems in a LAN, an intranet, an extranet, or the Internet. The computer system 600 may operate in the capacity of a server in a client-server network environment. The computer system 600 may be a personal computer (PC), a tablet computer, a set-top box (STB), a personal Digital Assistant (PDA), a mobile phone, a camera, a video camera, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The exemplary computer system 600 includes a processing device 602, a main memory 604 (e.g., read-only memory (ROM), flash memory, dynamic random access memory (DRAM) such as synchronous DRAM (SDRAM)), a static memory 606 (e.g., flash memory, static random access memory (SRAM)), and a data storage device 618, which communicate with each other via a bus 630.

Processing device 602 represents one or more general-purpose processing devices such as a microprocessor, central processing unit, or the like. More particularly, the processing device 602 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 602 may also be one or more special-purpose processing devices such as an application specific integrated circuit (ASIC), a field programmable gate array (FPGA), a digital signal processor (DSP), network processor, or the like. The processing device 602 is configured to execute instructions for performing the operations and steps discussed herein.

The computer system 600 may further include a network interface device 608. The computer system 600 also may include a video display unit 610 (e.g., a liquid crystal display (LCD) or a cathode ray tube (CRT)), an alphanumeric input device 612 (e.g., a keyboard), a cursor control device 614 (e.g., a mouse), and a signal generation device 616 (e.g., a speaker). In one illustrative example, the video display unit 610, the alphanumeric input device 612, and the cursor control device 614 may be combined into a single component or device (e.g., an LCD touch screen).

The data storage device 618 may include a computer-readable medium 628 on which the instructions 622 (e.g., implementing body movement analysis engine 112) embodying any one or more of the methodologies or functions described herein is stored. The instructions 622 may also reside, completely or at least partially, within the main memory 604 and/or within the processing device 602 during execution thereof by the computer system 600, the main memory 604 and the processing device 602 also constituting computer-readable media. The instructions 622 may further be transmitted or received over a network via the network interface device 608.

While the computer-readable storage medium 628 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

Although the operations of the methods herein are shown and described in a particular order, the order of the operations of each method may be altered so that certain operations may be performed in an inverse order or so that certain operation may be performed, at least in part, concurrently with other operations. In certain implementations, instructions or sub-operations of distinct operations may be in an intermittent and/or alternating manner.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

In the above description, numerous details are set forth. It will be apparent, however, to one skilled in the art, that the aspects of the present disclosure may be practiced without these specific details. In some instances, well-known structures and devices are shown in block diagram form, rather than in detail, in order to avoid obscuring the present disclosure.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "receiving," "determining," "selecting," "storing," "setting," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present disclosure also relates to an apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear as set forth in the description. In addition, aspects of the present disclosure are not described with reference to any particular programming language. It will be appreciated that a variety of programming languages may be used to implement the teachings of the present disclosure as described herein.

Aspects of the present disclosure may be provided as a computer program product, or software, that may include a machine-readable medium having stored thereon instructions, which may be used to program a computer system (or other electronic devices) to perform a process according to the present disclosure. A machine-readable medium includes any procedure for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.).

The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

What is claimed is:

1. A method comprising:
   receiving, from a three-dimensional (3D) motion capture system, initial data representing an initial orientation of a subject user's body in an initial position;
   receiving x-ray data representing at least the portion of the subject user's body in the initial position;
   determining an actual orientation of at least one bone or joint from the portion of the subject user's body in the initial position as represented in the x-ray data; and calibrating the initial orientation of the 3D motion capture system to reflect the actual orientation of the at least one bone or joint in the initial position, wherein calibrating the initial orientation of the 3D motion capture system to reflect the actual orientation of the at least one bone or joint in the initial position comprises replacing first values of tilt and rotation measured by the 3D motion capture system with second values of tilt and rotation determined from the x-ray data.

2. The method of claim 1, further comprising:
generating, from the x-ray data, an image of the portion of the subject user's body in the initial position; and
causing display of the image in an interface on a display device.

3. The method of claim 2, wherein determining the actual orientation of the at least one bone or joint in the initial position comprises:
receiving input via the interface, the input comprising an indication of the at least one bone or joint; and
determining an offset of the at least one bone or joint relative to a reference frame, wherein the offset represents the actual orientation of the at least one bone or joint in the initial position.

4. The method of claim 1, wherein receiving the initial data representing the initial orientation of the subject user's body comprises receiving the initial data from a plurality of 3D motion capture sensors affixed to at least a portion of the subject user's body.

5. The method of claim 4, further comprising:
receiving, from the plurality of 3D motion capture sensors, motion capture data associated with a movement of the subject user's body from the initial position to a subsequent position; and
analyzing the motion capture data associated with the subsequent position in relation to the actual orientation of the at least one bone or joint in the initial position.

6. The method of claim 5, wherein the motion capture data comprises one or more of positional data, rotational data, or acceleration data measured by the plurality of 3D motion capture sensors.

7. A system comprising:
a memory device storing instructions;
a processing device coupled to the memory device, the processing device to execute the instructions to perform operations comprising:
receiving, from a three-dimensional (3D) motion capture system, initial data representing an initial orientation of a subject user's body in an initial position;
receiving x-ray data representing at least the portion of the subject user's body in the initial position;
determining an actual orientation of at least one bone or joint from the portion of the subject user's body in the initial position as represented in the x-ray data; and
calibrating the initial orientation of the 3D motion capture system to reflect the actual orientation of the at least one bone or joint in the initial position, wherein calibrating the initial orientation of the 3D motion capture system to reflect the actual orientation of the at least one bone or joint in the initial position comprises replacing first values of tilt and rotation measured by the 3D motion capture system with second values of tilt and rotation determined from the x-ray data.

8. The system of claim 7, wherein the processing device to execute the instructions to perform further operations comprising:
generating, from the x-ray data, an image of the portion of the subject user's body in the initial position; and
causing display of the image in an interface on a display device.

9. The system of claim 8, wherein determining the actual orientation of the at least one bone or joint in the initial position comprises:
receiving input via the interface, the input comprising an indication of the at least one bone or joint; and
determining an offset of the at least one bone or joint relative to a reference frame, wherein the offset represents the actual orientation of the at least one bone or joint in the initial position.

10. The system of claim 7, wherein receiving the initial data representing the initial orientation of the subject user's body comprises receiving the initial data from a plurality of 3D motion capture sensors affixed to at least a portion of the subject user's body.

11. The system of claim 7, wherein the processing device to execute the instructions to perform further operations comprising:
receiving, from the plurality of 3D motion capture sensors, motion capture data associated with a movement of the subject user's body from the initial position to a subsequent position; and
analyzing the motion capture data associated with the subsequent position in relation to the actual orientation of the at least one bone or joint in the initial position.

12. The system of claim 11, wherein the motion capture data comprises one or more of positional data, rotational data, or acceleration data measured by the plurality of 3D motion capture sensors.

13. A non-transitory computer-readable storage medium storing instructions that, when executed by a processing device, cause the processing device to perform operations comprising:
receiving, from a three-dimensional (3D) motion capture system, initial data representing an initial orientation of a subject user's body in an initial position;
receiving x-ray data representing at least the portion of the subject user's body in the initial position;
determining an actual orientation of at least one bone or joint from the portion of the subject user's body in the initial position as represented in the x-ray data; and
calibrating the initial orientation of the 3D motion capture system to reflect the actual orientation of the at least one bone or joint in the initial position, wherein calibrating the initial orientation of the 3D motion capture system to reflect the actual orientation of the at least one bone or joint in the initial position comprises replacing first values of tilt and rotation measured by the 3D motion capture system with second values of tilt and rotation determined from the x-ray data.

14. The non-transitory computer-readable storage medium of claim 13, wherein the instructions cause the processing device to perform further operations comprising:
generating, from the x-ray data, an image of the portion of the subject user's body in the initial position; and
causing display of the image in an interface on a display device.

15. The non-transitory computer-readable storage medium of claim 14, wherein determining the actual orientation of the at least one bone or joint in the initial position comprises:

receiving input via the interface, the input comprising an indication of the at least one bone or joint; and determining an offset of the at least one bone or joint relative to a reference frame, wherein the offset represents the actual orientation of the at least one bone or joint in the initial position.

16. The non-transitory computer-readable storage medium of claim 13, wherein receiving the initial data representing the initial orientation of the subject user's body comprises receiving the initial data from a plurality of 3D motion capture sensors affixed to at least a portion of the subject user's body.

17. The non-transitory computer-readable storage medium of claim 16, wherein the instructions cause the processing device to perform further operations comprising:

receiving, from the plurality of 3D motion capture sensors, motion capture data associated with a movement of the subject user's body from the initial position to a subsequent position; and analyzing the motion capture data associated with the subsequent position in relation to the actual orientation of the at least one bone or joint in the initial position.

* * * * *